United States Patent
Yoshimoto et al.

(10) Patent No.: US 11,906,425 B2
(45) Date of Patent: Feb. 20, 2024

(54) SIMULATION SAMPLE DESIGN METHOD, SIMULATION SAMPLE MANUFACTURING METHOD, SIMULATION SAMPLE DESIGN DEVICE, PROGRAM, AND RECORDING MEDIUM

(71) Applicant: HAMAMATSU PHOTONICS K.K., Hamamatsu (JP)

(72) Inventors: Kenji Yoshimoto, Hamamatsu (JP); Yukio Ueda, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 141 days.

(21) Appl. No.: 17/615,896

(22) PCT Filed: Jun. 1, 2020

(86) PCT No.: PCT/JP2020/021596
§ 371 (c)(1),
(2) Date: Dec. 2, 2021

(87) PCT Pub. No.: WO2020/255685
PCT Pub. Date: Dec. 24, 2020

(65) Prior Publication Data
US 2022/0317036 A1    Oct. 6, 2022

(30) Foreign Application Priority Data
Jun. 19, 2019  (JP) .................. 2019-113864

(51) Int. Cl.
*G01N 21/359* (2014.01)
*G01N 21/3563* (2014.01)
(Continued)

(52) U.S. Cl.
CPC ......... *G01N 21/359* (2013.01); *G01N 21/278* (2013.01); *G01N 21/3563* (2013.01);
(Continued)

(58) Field of Classification Search
CPC ............... G01N 21/359; G01N 21/278; G01N 21/3563; G01N 33/442; G01N 2201/121;
(Continued)

(56) References Cited

U.S. PATENT DOCUMENTS

2014/0303496 A1* 10/2014 Hasegawa ............ G01N 21/278
600/431
2019/0105846 A1*  4/2019 Hanano ................. B29C 64/393

FOREIGN PATENT DOCUMENTS

JP    2001-008941 A    1/2001
JP    2004-261364 A    9/2004
(Continued)

OTHER PUBLICATIONS

Ayers et al., Fabrication and characterization of silicone-based tissue phantoms with tunable optical properties in the visible and near infrared domain, 2008, Proc. of SPIE vol. 6870, pp. 68700-1 to 687007-9 (Year: 2008).*

(Continued)

*Primary Examiner* — Christine S. Kim
(74) *Attorney, Agent, or Firm* — Faegre Drinker Biddle & Reath LLP

(57) ABSTRACT

A phantom design method includes a correction step and a calculation step. In the correction step, an absorption spectrum of a target of spectroscopic measurement by a near infrared spectrometer is corrected based on a refractive index of the target and a refractive index of a resin used as a base material of a phantom to generate a corrected absorption spectrum. In the calculation step, based on an absorption spectrum of the resin and an absorption spectrum of each of N types of dyes, a concentration of each of the N types of dyes to be contained in the base material is calculated such that an absorption spectrum of the phantom constituted by the base material containing the N types of (Continued)

dyes approximates the corrected absorption spectrum in a predetermined wavelength range of a near infrared region.

13 Claims, 10 Drawing Sheets

(51) Int. Cl.
  *G01N 33/44*     (2006.01)
  *G01N 21/27*     (2006.01)
(52) U.S. Cl.
  CPC ..... *G01N 33/442* (2013.01); *G01N 2201/121* (2013.01); *G01N 2201/13* (2013.01)
(58) Field of Classification Search
  CPC ........... G01N 2201/13; G01N 21/4785; G01N 2201/129; A61B 5/1495; A61B 5/1455
  See application file for complete search history.

(56) References Cited

FOREIGN PATENT DOCUMENTS

JP          6083801 B2 *   2/2017
JP          2017-148223 A   8/2017

OTHER PUBLICATIONS

Ntombela et al., Low-cost fabrication of optical tissue phantoms for use in biomedical imaging, 2020, J.heliyon pp. 1-8 (Year: 2020).*

International Preliminary Report on Patentability dated Dec. 30, 2021 for PCT/JP2020/021596.
Akl, Tony J. et al., "Optimizing probe design for an implantable perfusion and oxygenation sensor," Biomedical Optics Express, Aug. 1, 2011, vol. 2, No. 8, pp. 2096-2109.
Boecklin, C. et al., "Mixing formula for tissue-mimicking silicone phantoms in the near infrared," Journal of Physics D: Applied Physics, vol. 48, No. 10, 2015, pp. 105402-1-105402-6.
Jang, Hyounguk et al., "Oximetry system performance assessment with POM (acetal) phantoms incorporating hemoglobin calibration standards and customized saturation levels," Proceedings of SPIE, vol. 9315, 2015, p. 931503-1-p. 931503-7.
Swartling, J. et al., "Rigorous characterization of time-resolved diffuse spectroscopy systems for measurements of absorption and scattering properties using solid phantoms," Proceedings of SPIE, vol. 5138, 2003, pp. 80-87.
Tanigawa (Takahashi), Yukari, "Manufacturing of optical organism simulation samples in research and development of optical CT," Optical Alliance, vol. 8, No. 2, 1997, pp. 18-22.
Walter, Alec et al., "Development of breast cancer tissue phantoms for terahertz imaging," Proceedings of SPIE, vol. 9700, 2016, p. 970003-1-p. 970003-8.
Hebden J. C. Et al., "Time-resolved optical imaging of a solid tissue-equivalent phantom", Applied Optics, Optical Society of America, Washington, DC, US, vol. 34, No. 34, Dec. 1, 1995, p. 8038-p. 8047, XP001149959.
Firbank M. et al., "An improved design for a stable and reproducible phantom material for use in near-infrared spectroscopy and imaging", Physics in Medicine and Biology, Institute of Physics Publishing, Bristol GB, vol. 40, No. 5, Jan. 1, 1995, p. 955-p. 961, XP007910748.

* cited by examiner

Fig.6

| | ABSORPTION COEFFICIENT (1/cm) | | | O2Hb (μM) | HHb (μM) | tHb (μM) | StO2 (%) |
| --- | --- | --- | --- | --- | --- | --- | --- |
| | 760nm | 800nm | 830nm | | | | |
| TARGET | 0.0658 | 0.0559 | 0.0673 | 18.0 | 7.0 | 25.0 | 72.0 |
| MEASUREMENT RESULT | 0.0652 | 0.0556 | 0.0681 | 17.6 | 6.9 | 24.5 | 71.7 |

Fig.8

| | ABSORPTION COEFFICIENT (1/cm) | | | O2Hb (μM) | HHb (μM) | tHb (μM) | StO2 (%) |
|---|---|---|---|---|---|---|---|
| | 760nm | 800nm | 830nm | | | | |
| TARGET | 0.1720 | 0.1507 | 0.1745 | 47.0 | 23.0 | 70.0 | 67.1 |
| MEASUREMENT RESULT | 0.1716 | 0.1494 | 0.1781 | 45.6 | 23.3 | 68.9 | 66.2 |

Fig. 10

| | ABSORPTION COEFFICIENT (1/cm) | | | O2Hb (μM) | HHb (μM) | tHb (μM) | StO2 (%) |
|---|---|---|---|---|---|---|---|
| | 760nm | 800nm | 830nm | | | | |
| TARGET | 0.2186 | 0.1496 | 0.1627 | 28.0 | 42.0 | 70.0 | 40.0 |
| MEASUREMENT RESULT | 0.2156 | 0.1519 | 0.1669 | 29.5 | 41.1 | 70.6 | 41.8 |

SIMULATION SAMPLE DESIGN METHOD, SIMULATION SAMPLE MANUFACTURING METHOD, SIMULATION SAMPLE DESIGN DEVICE, PROGRAM, AND RECORDING MEDIUM

TECHNICAL FIELD

The present disclosure relates to a method and an apparatus for designing a phantom used in evaluating performance of a near infrared spectrometer.

BACKGROUND ART

A near infrared spectrometer (NIRS: near infrared spectroscopy) capable of measuring a hemoglobin concentration, a tissue oxygen saturation, and the like of a living tissue from a light absorption property obtained when a living body is irradiated with near infrared light in a wavelength region of approximately 700 nm to 1100 nm is known. In the spectroscopic measurement by time resolved spectroscopy (TRS) using the near infrared spectrometer, the living body, being a target of the spectroscopic measurement, is irradiated with short pulsed light of a near infrared region, diffused light emitted to the outside of the living body by diffusing the short pulsed light inside the living body is detected, and the hemoglobin concentration, the tissue oxygen saturation, and the like of the living tissue can be measured based on a time response waveform of the detected diffused light, and further, images of distributions of the above values can be obtained.

A phantom (simulated sample) is used in evaluating performance (measurement accuracy, reproducibility, stability, and the like) of the near infrared spectrometer. The phantom is required to have an optical property close to the optical property of the target of the spectroscopic measurement. Further, for evaluating the reproducibility and the long-term stability of the near infrared spectrometer, it is desirable that the temporal variation of the optical property of the phantom is small. Conventionally, resin, water, gelatin, agar (water base), oil (lard, butter) and the like have been used as materials for a base material of the phantom.

In the above materials of the base material, a resin is preferable in that the temporal variation of the optical property is small, handling is easy, and the like. Patent Document 1 describes an invention of the phantom using the resin as the base material. The phantom is used for evaluation of basic properties such as measurement accuracy at each wavelength of the near infrared spectrometer in many cases, and thus, a dye (for example, carbon ink) having no large change in an absorption spectrum in the near infrared region is contained in the base material. As the wavelength becomes longer in the near infrared region, the absorption of the carbon ink monotonically decreases. Therefore, it is difficult for this phantom to reproduce the absorption spectrum of the living tissue.

On the other hand, when the hemoglobin concentration, the tissue oxygen saturation, and the like of the living tissue are measured using the near infrared spectrometer or the variations of these values are observed, in general, a liquid phantom obtained by adding actual blood to a lipid emulsion diluted with distilled water is used. This phantom can accurately reproduce the absorption spectrum of the living tissue. However, since this phantom uses actual blood, it is not preferable in view of hygiene problems caused by handling blood and complexity of the experimental system.

CITATION LIST

Patent Literature

Patent Document 1: Japanese Patent Application Laid-Open Publication No. 2017-148223

SUMMARY OF INVENTION

Technical Problem

If there is a phantom that can reproduce the absorption spectrum of the target of spectroscopic measurement with high accuracy and uses a resin as the base material, it is possible to easily evaluate the reproducibility and the long-term stability of the near infrared spectrometer by using the phantom, and it is considered to be very useful in developing the near infrared spectrometer.

However, the present inventors made a phantom that reproduces the absorption spectrum of the target of spectroscopic measurement by way of trial by containing a dye of an appropriate type with an appropriate concentration in a resin serving as a base material, and attempted to perform evaluation of performance of the near infrared spectrometer using the phantom, and found that a good evaluation result cannot be obtained.

An object of an embodiment is to provide a phantom design method and a phantom design apparatus capable of designing a phantom suitably used in evaluating performance of a near infrared spectrometer, a method for preparing the phantom, a program of the phantom design method, and a recording medium recording the program.

Solution to Problem

An embodiment is a phantom design method. The phantom design method is a method for designing a phantom used in evaluating performance of a near infrared spectrometer, and includes (1) a correction step of correcting an absorption spectrum of a target of spectroscopic measurement by the near infrared spectrometer based on a refractive index of the target and a refractive index of a resin used as a base material of the phantom to generate a corrected absorption spectrum; and (2) a calculation step of calculating, based on an absorption spectrum of the resin and an absorption spectrum of each of N types of dyes, N being 2 or more, a concentration of each of the N types of dyes to be contained in the base material such that an absorption spectrum of the phantom constituted by the base material containing the N types of dyes approximates the corrected absorption spectrum in a predetermined wavelength range of a near infrared region.

An embodiment is a phantom preparation method. The phantom preparation method includes calculating the concentration of each of the N types of dyes in the base material by the phantom design method of the above configuration; and preparing the phantom by causing the base material to contain the N types of dyes according to the calculated concentrations.

An embodiment is a program. The program is a program for causing a computer to execute the correction step and the calculation step of the phantom design method of the above configuration. Further, an embodiment is a recording medium. The recording medium is a computer readable recording medium recording the above program.

An embodiment is a phantom design apparatus. The phantom design apparatus is an apparatus for designing a phantom used in evaluating performance of a near infrared spectrometer, and includes (1) a correction unit for correcting an absorption spectrum of a target of spectroscopic measurement by the near infrared spectrometer based on a refractive index of the target and a refractive index of a resin used as a base material of the phantom to generate a corrected absorption spectrum; and (2) a calculation unit for calculating, based on an absorption spectrum of the resin and an absorption spectrum of each of N types of dyes, N being 2 or more, a concentration of each of the N types of dyes to be contained in the base material such that an absorption spectrum of the phantom constituted by the base material containing the N types of dyes approximates the corrected absorption spectrum in a predetermined wavelength range of a near infrared region.

Advantageous Effects of Invention

According to the phantom design method, the phantom preparation method, the phantom design apparatus, the program, and the recording medium of the embodiments, a phantom suitably used in evaluating performance of a near infrared spectrometer can be designed and prepared.

BRIEF DESCRIPTION OF DRAWINGS

FIG. 6 is a table showing an absorption coefficient at each wavelength, an oxygenated hemoglobin concentration ($O_2Hb$), a deoxygenated hemoglobin concentration (HHb), a total hemoglobin concentration (tHb), and a tissue oxygen saturation ($StO_2$) for each of the target (breast) and the actually prepared phantom.

FIG. 8 is a table showing the absorption coefficient at each wavelength, the oxygenated hemoglobin concentration ($O_2Hb$), the deoxygenated hemoglobin concentration (HHb), the total hemoglobin concentration (tHb), and the tissue oxygen saturation ($StO_2$) for each of the target (head of normal-oxygen condition) and the actually prepared phantom.

FIG. 10 is table showing the absorption coefficient at each wavelength, the oxygenated hemoglobin concentration ($O_2Hb$), the deoxygenated hemoglobin concentration (HHb), the total hemoglobin concentration (tHb), and the tissue oxygen saturation ($StO_2$) for each of the target (head of low-oxygen condition) and the actually prepared phantom.

DESCRIPTION OF EMBODIMENTS

Hereinafter, embodiments of a phantom design method, a phantom preparation method, a phantom design apparatus, a program, and a recording medium will be described in detail with reference to the accompanying drawings. In the description of the drawings, the same elements will be denoted by the same reference signs, and redundant description will be omitted. The present invention is not limited to these examples.

Figure 1:
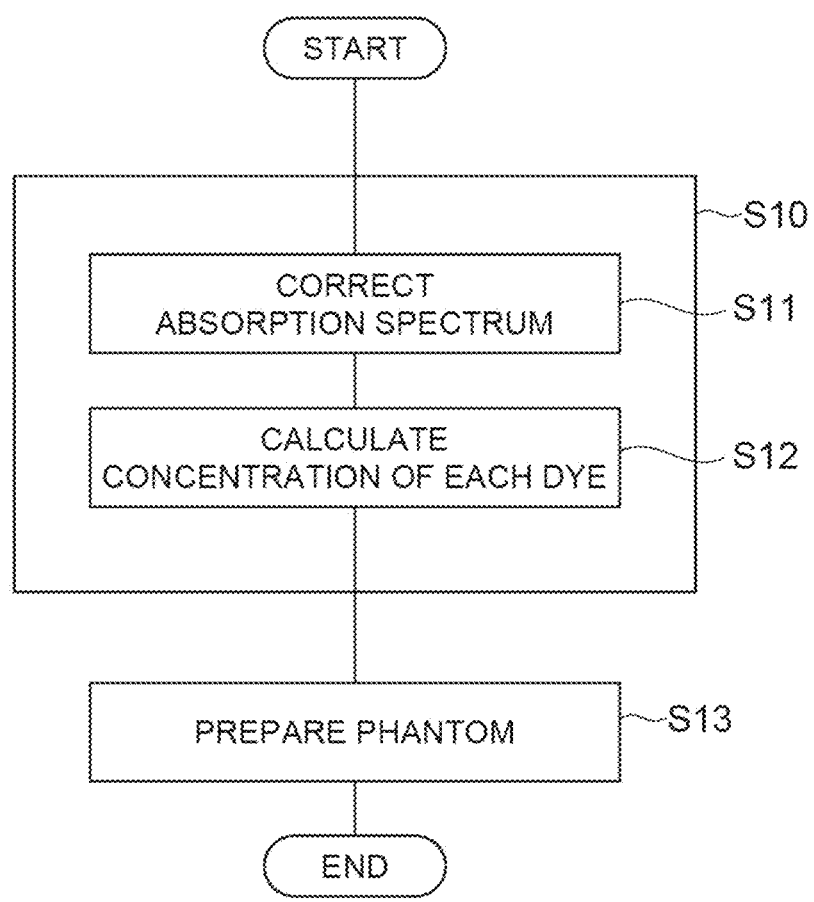
FIG. 1 is a flowchart of a phantom design method and a phantom preparation method.

FIG. 1 is a flowchart illustrating a phantom design method and a phantom preparation method. The phantom design method includes a correction step S11 and a calculation step S12. The phantom preparation method includes a design step S10 including the correction step S11 and the calculation step S12, and a preparation step S13. A phantom to be designed and prepared uses a resin as a base material, and contains N types of dyes, N being 2 or more, in the base material, and further, preferably contains scattering particles.

In the correction step S11, first, a target of spectroscopic measurement by a near infrared spectrometer, a resin used as the base material of the phantom, and the N types of dyes to be contained in the base material are determined. Then, an absorption spectrum of the target of the spectroscopic measurement is corrected based on a refractive index of the target and a refractive index of the resin to generate a corrected absorption spectrum. Details of the correction will be described later.

The target of the spectroscopic measurement can be arbitrarily selected, and is, for example, a living tissue such as a breast, a head, a muscle of leg or arm, and the like. A hemoglobin amount, a water amount, and a lipid amount are different depending on a region of the target. Therefore, the absorption spectrum of the target varies depending on the target, and may vary, in some cases, depending on a state of the target. The resin and the dyes are determined according to the target.

The resin used as the base material of the phantom may be in a cured state or may be used in a liquid state. When the cured resin is used as the base material, the resin is cured after mixing the dyes and the scattering particles. As the resin, various resins such as an epoxy resin, a polyurethane resin, a silicone rubber, and the like can be used. Further, the resin may be cured by any curing method such as one-component curing type, two-component mixing type, ultraviolet curing type, or thermal curing type. It is desirable to use a resin having a transmittance of 95% or more in a wavelength region of approximately 700 nm to 1100 nm.

As the N types of dyes, the dyes with which the absorption spectrum of the phantom can accurately approximate the absorption spectrum of the target by appropriately setting the concentration of each dye in the base material (resin) are used. For example, when the target is a living tissue, a dye A and a dye B in the N types of dyes can be set as follows.

The dye A is selected such that the phantom can reproduce the light absorption property of the deoxygenated hemoglobin (HHb) by itself or by mixing with other dyes. As the dye A, a dye having an absorption peak in the vicinity of 760 nm, which is the same as that of the deoxygenated hemoglobin, in the near infrared region of a wavelength of 700 nm to 1100 nm is desirable, and various dyes such as FDN-001 manufactured by Yamada Chemical, IRA 761 manufactured by Exciton, and the like can be used.

The dye B is selected such that the phantom can reproduce the light absorption property of the oxygenated hemoglobin ($O_2Hb$) by itself or by mixing with other dyes. As the dye B, a dye with an absorption gradually increasing toward a long wavelength side from a wavelength of 700 nm, which is the same as that of the oxygenated hemoglobin, and having an absorption peak in the vicinity of a wavelength of 900 nm, in the near infrared region of a wavelength of 700 nm to 1100 nm is desirable, and various dyes such as Pro-Jet 900NP manufactured by Fujifilm, IRA 912, IRA 931 manufactured by Exciton, and the like can be used.

The scattering particles are added to the base material for reproducing the light scattering property close to the target in the phantom. As the scattering particles, various materials such as titanium oxide ($TiO_2$), aluminium oxide ($Al_2O_3$), silica particles ($SiO_2$), silicon powders (Si), acrylic powders, and the like may be used. The diameter of the scattering particle is desirably about 0.01 µm to 10 µm.

The phantom may have a plurality of regions having different absorption spectra. For example, an inner region of the phantom and a peripheral region surrounding the inner region may have different absorption spectra. In this case, for each region, the processing of the correction step S11 is performed, and the processing of the calculation step S11 and the subsequent steps is performed. In this way, it is possible to realize a phantom capable of reproducing a state close to the actual measurement, for example, such as a cancer tissue in a normal tissue, a pathological condition such as variations in hemoglobin concentration or tissue oxygen saturation in a living body, and variations in a living tissue.

In the calculation step S12, based on the absorption spectrum of the resin and the absorption spectrum of each of the N types of dyes, the concentration of each of the N types of dyes to be contained in the base material is calculated such that the absorption spectrum of the phantom constituted by the base material containing the N types of dyes approximates the corrected absorption spectrum in a predetermined wavelength range of the near infrared region. Further, the predetermined wavelength range is a wavelength range used in the spectroscopic measurement of the target, and includes, for example, a range of 750 nm to 850 nm when the target is a living tissue.

The least squares method can be used for calculating the concentration of each dye. That is, the absorption coefficient of the resin at the wavelength $\lambda$ is represented by $\mu^\lambda_{a,resin}$. The absorption coefficient of the n-th dye in the N types of dyes per unit concentration at the wavelength $\lambda$ is represented by $\varepsilon^\lambda_{a,n}$, and the concentration of the n-th dye is represented by $C_n$. Further, the value of the corrected absorption spectrum at the wavelength $\lambda$ is represented by $\mu^\lambda_{a,tissue}$.

The absorption coefficient $\mu^\lambda_{a,phantom}(C)$ of the phantom at the wavelength $\lambda$ is represented by the following Formula (1). Further, the concentrations $C_1$ to $C_N$ are calculated such that F(C) represented by the following Formula (2) is minimized (or becomes smaller than a predetermined threshold value). The summation of the right side of the Formula (2) is calculated for each wavelength in the predetermined wavelength range of the near infrared region.

[Formula 1]

$$\mu^\lambda_{a,phantom}(C) = \mu^\lambda_{a,resin} + \sum_{n=1}^{N} \varepsilon^\lambda_{a,n} C_n \quad (1)$$

[Formula 2]

$$F(C) = \sum_\lambda [\mu^\lambda_{a,phantom}(C) - \mu^\lambda_{a,tissue}]^2 \quad (2)$$

In the calculation step S12, a coincidence degree between the absorption spectrum of the phantom constituted by the base material containing the N types of dyes with the calculated concentrations and the corrected absorption spectrum may be obtained. The coincidence degree is, for example, represented by the above Formula (2).

Further, in the calculation step S12, it is preferable to calculate, for each group including any N types of dyes out of M types of dyes, M being 3 or more, the concentration of each of the N types of dyes to be contained in the base material and obtain the coincidence degree, and select the N types of dyes and the concentrations of any one group based on the number of types of dyes and the coincidence degree of each group. As the number of types of dyes contained in the base material increases, the preparation of the phantom becomes more complicated, and therefore, when the desired coincidence degree is obtained, it is preferable that the number of types of dyes is small. Further, when the desired coincidence degree cannot be obtained unless the number of types of dyes contained in the base material is increased, the types of dyes must be increased.

In the preparation step S13, the phantom is prepared by causing the base material (resin) to contain the N types of dyes according to the concentrations calculated in the calculation step S12. At this time, the phantom may be prepared by causing the base material to contain the scattering particles in addition to the N types of dyes.

Figure 2:
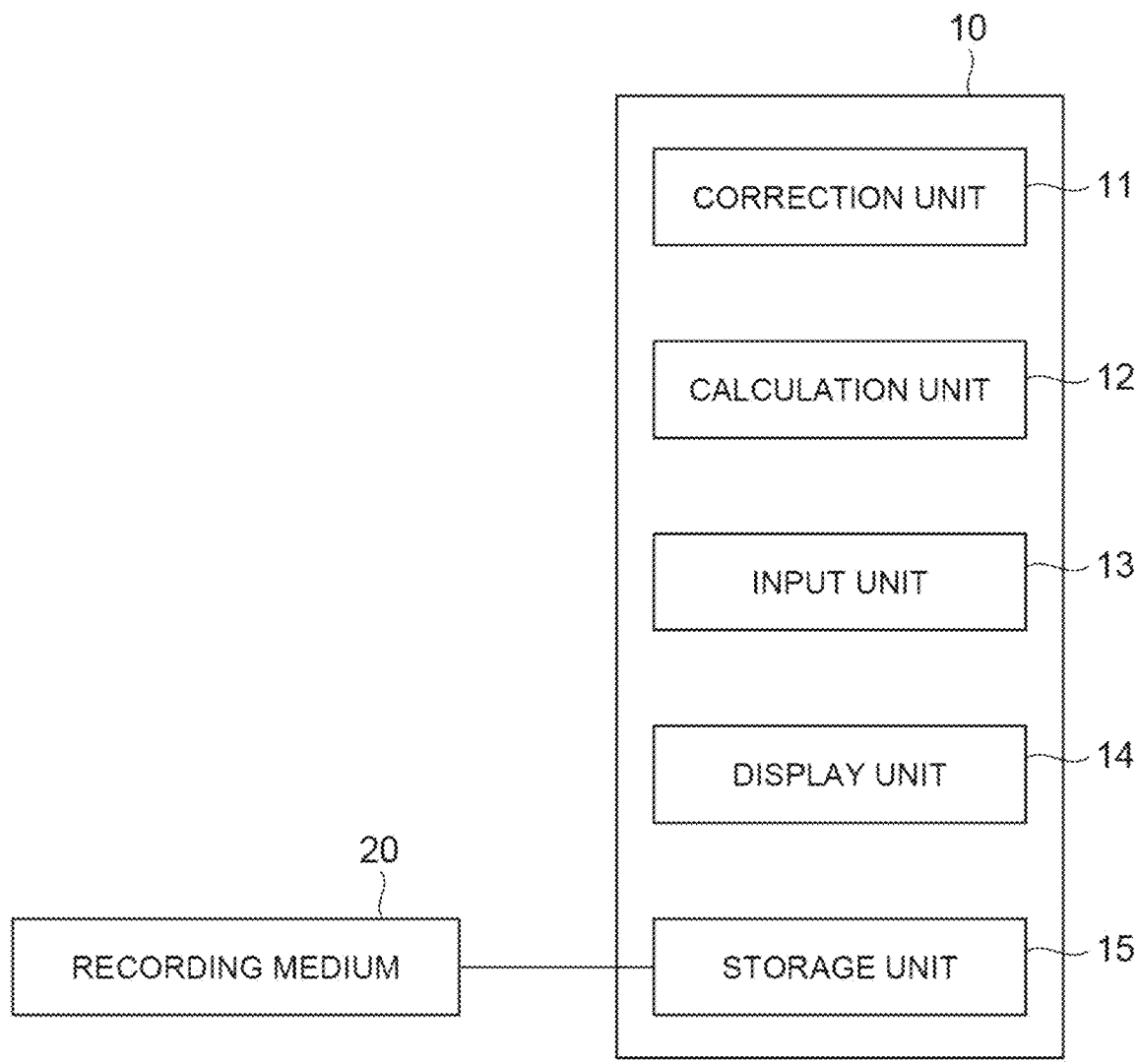
FIG. 2 is a diagram illustrating a configuration of a phantom design apparatus.

FIG. 2 is a diagram illustrating a configuration of a phantom design apparatus 10. The phantom design apparatus 10 includes a correction unit 11, a calculation unit 12, an input unit 13, a display unit 14, and a storage unit 15. The phantom design apparatus 10 may be configured by a computer. The correction unit 11 performs the processing of the correction step S11, and the calculation unit 12 performs the processing of the calculation step S12. The correction unit 11 and the calculation unit 12 include a processor such as a CPU. The input unit 13 receives input of information necessary for the processing by the correction unit 11 and the calculation unit 12 (for example, information on the target of the spectroscopic measurement, the resin, the dyes, the wavelength range, and the like), and includes, for example, a keyboard and a mouse.

The display unit 14 displays various types of information (for example, the absorption spectrum of the target, the corrected absorption spectrum, the absorption spectrum of the phantom, and the like), and includes, for example, a liquid crystal display. The storage unit 15 stores programs and various types of information, and includes, for example, a hard disk drive, a RAM, and a ROM. The programs stored in the storage unit 15 include a program (hereinafter referred to as an "execution program") that causes the correction unit 11 to execute the processing of the correction step S11 and causes the calculation unit 12 to execute the processing of the calculation step S12.

The execution program may be stored in the storage unit 15 at the time of shipment of the phantom design apparatus 10, may be acquired via a communication line after shipment and then stored in the storage unit 15, or may be recorded in the computer readable recording medium 20 and then stored in the storage unit 15. The recording medium 20 may be any medium such as a flexible disk, a CD-ROM, a DVD-ROM, a BD-ROM, a USB memory, or the like.

Figure 3:
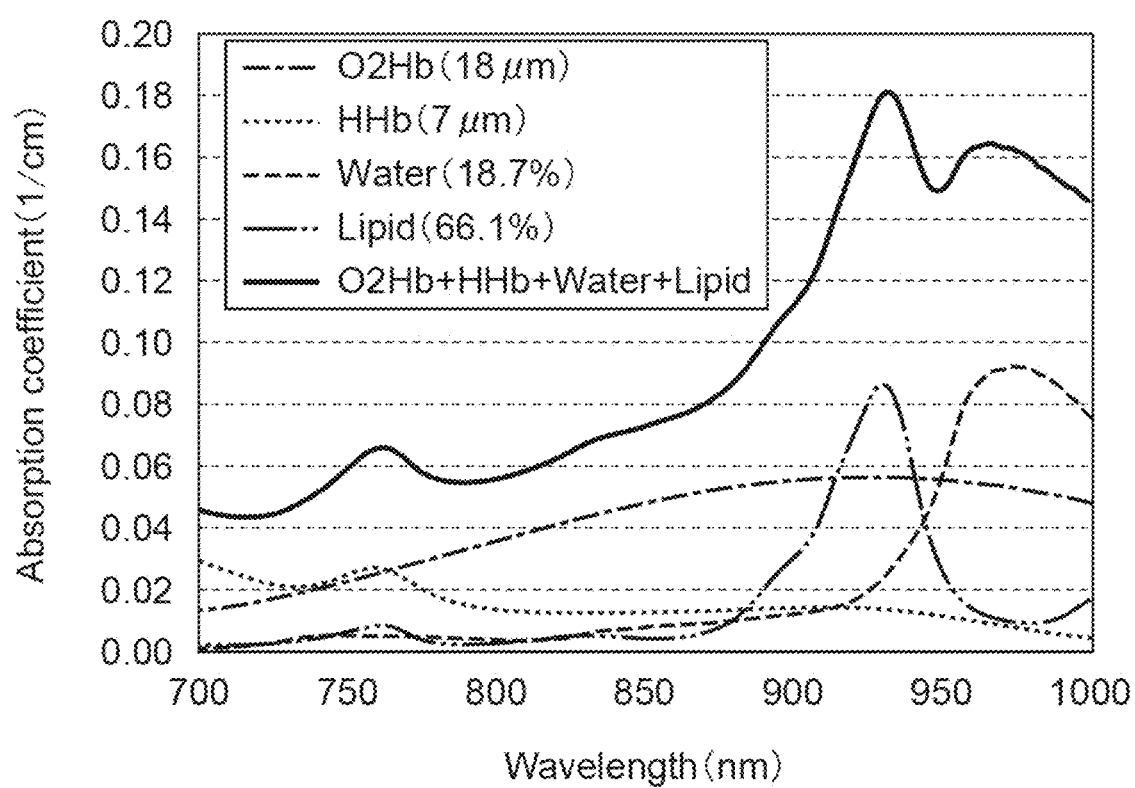
FIG. 3 is a diagram showing absorption spectra of a breast and respective components.

Hereinafter, the phantom design method will be described in more detail for the case where the target of the spectroscopic measurement is a human breast. The human breast generally contains 18 µM oxygenated hemoglobin ($O_2Hb$), 7 µM deoxygenated hemoglobin (HHb), 18.7% water, and 66.1% lipid. FIG. 3 is a diagram showing absorption spectra of the breast and the respective components. The absorption spectrum of the breast is the sum of the absorption spectra of the respective components. First, the design of the phantom capable of reproducing the absorption spectrum of the breast will be described.

A two-component mixing type epoxy resin (main agent: Araldite DBF, curing agent: XD716) is used as the resin being the base material of the phantom. FDN-001 manufactured by Yamada Chemical is used as the dye A that mainly reproduces the light absorption property of the deoxygenated hemoglobin (HHb). Pro-Jet 900NP manufactured by Fujifilm is used as the dye B that mainly reproduces the light absorption property of the oxygenated hemoglobin ($O_2Hb$). Further, as a dye C, CB #900 manufactured by Mitsubishi Chemical is used. In addition, the dye C has a small contribution in reproducing the absorption spectrum of the breast, but is necessary for reproducing the absorption spectrum of a head or a muscle.

Figure 4:
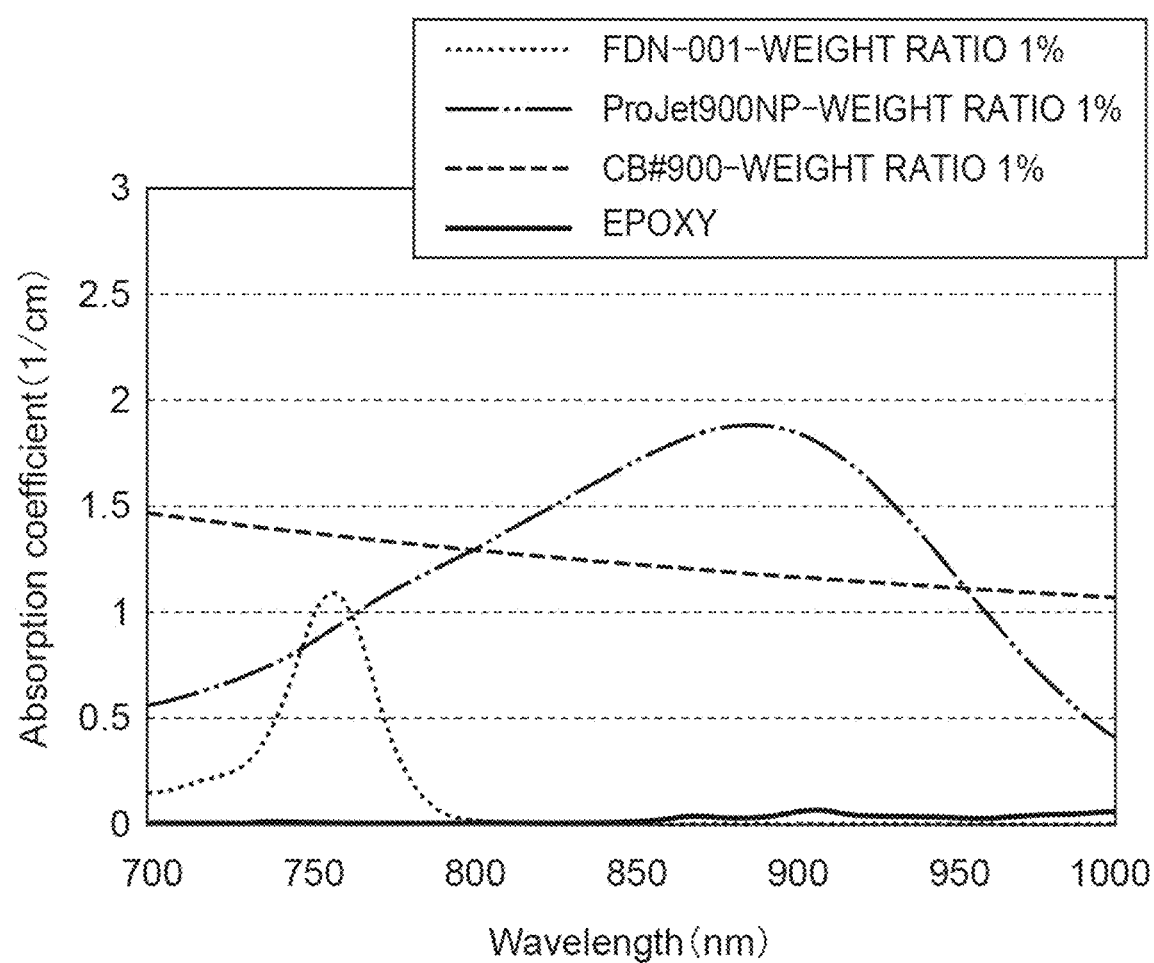
FIG. 4 is a diagram showing absorption spectra of an epoxy resin and dyes A to C.

FIG. 4 is a diagram showing absorption spectra of the epoxy resin and the dyes A to C. The absorption spectrum of each dye is an absorption spectrum of the epoxy resin containing the dye of a unit contained amount (weight ratio 1%). In addition, instead of using the dyes A to C as they are, for the purpose of facilitating the adjustment of the contained amount of the dye in the resin, an agent in which the dye of the unit contained amount (weight ratio 1%) is dissolved in the main agent of the epoxy resin is prepared in advance. Hereinafter, these are referred to as the dyes A to C.

For designing the phantom capable of reproducing the absorption spectrum of the target of the spectroscopic measurement, based on the absorption coefficient of the target at each of a plurality of wavelengths in a wavelength range of 750 nm to 850 nm, the concentration (% weight ratio) of each of the dyes A to C in the resin is calculated by the least squares method or the like so as to approach the absorption coefficients (calculation step).

When the target of the spectroscopic measurement is the breast, the absorption coefficient at a wavelength of 760 nm is 0.0658/cm, the absorption coefficient at a wavelength of 800 nm is 0.0559/cm, and the absorption coefficient at a wavelength of 830 nm is 0.0673/cm. When the concentration of each dye capable of reproducing the absorption spectrum of the target is calculated, the concentration of the dye A is 0.0206%, the concentration of the dye B is 0.0378%, and the concentration of the dye C is approximately 0%. In the phantom prepared by containing the respective dyes in the epoxy resin according to the above concentrations, the absorption coefficient at a wavelength of 760 nm is 0.0658/cm, the absorption coefficient at a wavelength of 800 nm is 0.0573/cm, and the absorption coefficient at a wavelength of 830 nm is 0.0661/cm.

Figure 5:
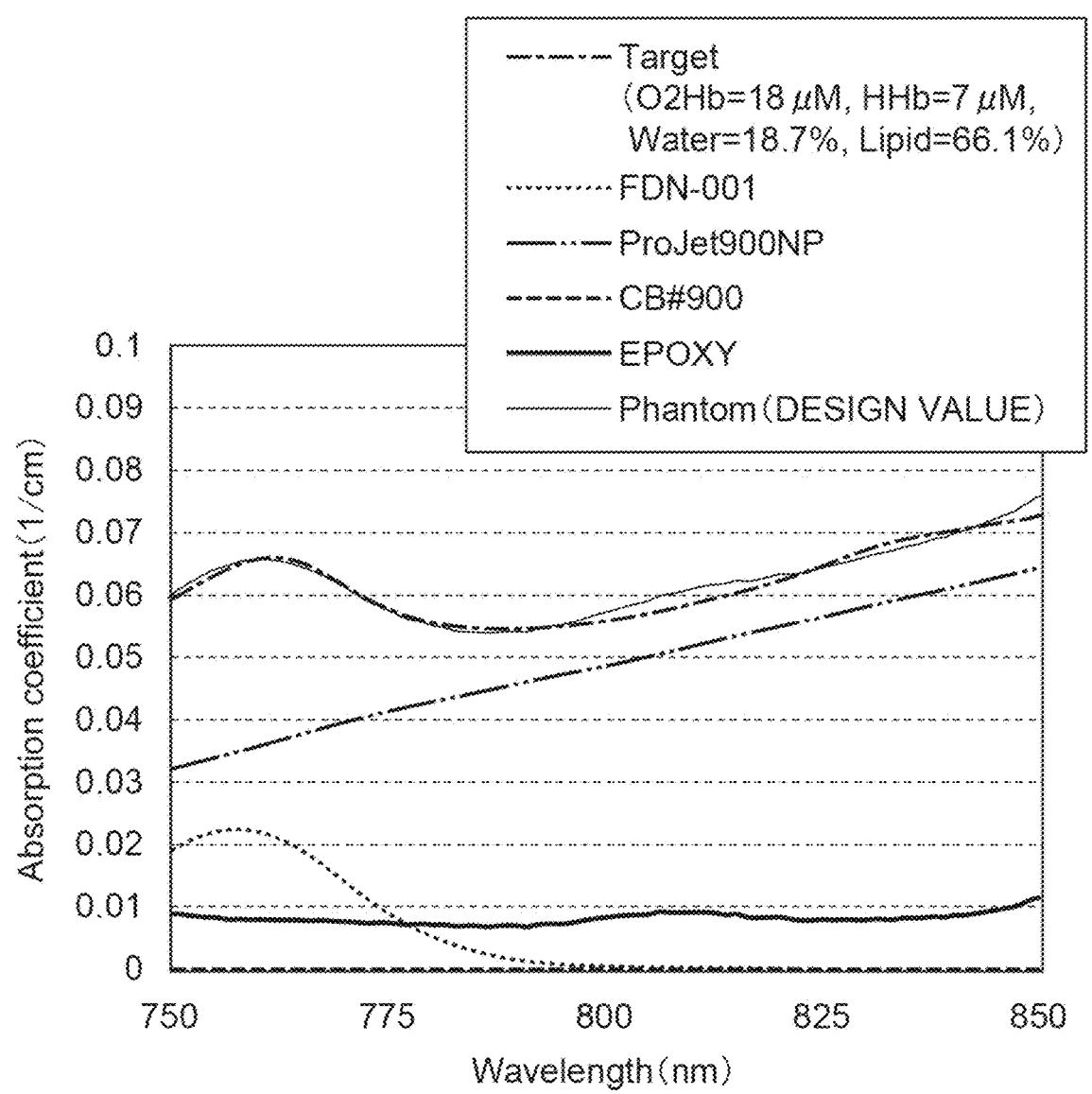
FIG. 5 is a diagram showing absorption spectra of a target (breast), a phantom, the epoxy resin, and the dyes A to C.

FIG. 5 is a diagram showing absorption spectra of the target (breast), the phantom, the epoxy resin, and the dyes A to C. As shown in this figure, the absorption spectra of the target (breast) and the phantom are in good agreement with each other.

However, in the spectroscopic measurement by the TRS method using the near infrared spectrometer, since a time response waveform of diffused light output from the target is measured with respect to irradiation of short pulsed light to the target, it is necessary to consider that the refractive index $n_{tissue}$ of the target is different from the refractive index $n_{resin}$ of the resin. The refractive index $n_{tissue}$ of the target varies depending on the region, and is about 1.36 on average. The refractive index $n_{resin}$ of the epoxy resin is 1.56. Due to the above difference in the refractive index, when an attempt is made to achieve evaluation of performance of the near infrared spectrometer using the phantom, a good evaluation result cannot be obtained.

Therefore, in the correction step prior to the calculation step, the absorption spectrum of the target is corrected based on the refractive index $n_{tissue}$ of the target of the spectroscopic measurement and the refractive index $n_{resin}$ of the resin to generate the corrected absorption spectrum. Further, in the calculation step, the concentration of each dye is calculated based on the corrected absorption spectrum. The processing contents in the correction step are as follows.

In general, the absorption of light by a material can be expressed by the Beer-Lambert law. It is assumed that a light intensity at the time of incidence on the material is $I_0$, a distance that the light passes through the material is L, a light intensity at the time of output from the material is I, and an absorption coefficient of the material is $\mu_a$. There is a relationship of the following Formula (3) between these parameters. It is assumed that a light speed in the material is c, and a time required for the light to pass through the material is t. Since the distance L is the product of the light speed c and the time t, the Formula (3) becomes the following Formula (4).

$$I = I_0 \exp(-\mu_a L) \quad \text{(Formula 3)}$$

$$I = I_0 \exp(-\mu_a c t) \quad \text{(Formula 4)}$$

The light speed c in the material depends on a refractive index n of the material. It is assumed that a light speed in the vacuum is $c_0$, and a refractive index of the vacuum is $n_0$. The light speed $c_{tissue}$ in the target is represented by the following Formula (5). The light speed $c_{resin}$ the resin is represented by the following Formula (6).

$$c_{tissue} = c_0(n_0/n_{tissue}) \quad \text{(Formula 5)}$$

$$c_{resin} = c_0(n_0/n_{resin}) \quad \text{(Formula 6)}$$

When the material through which the light passes is the resin (absorption coefficient $\mu_{a,resin}$, refractive index $n_{resin}$, light speed $c_{resin}$), the above Formula (4) becomes the following Formula (7). Further, when the phantom with the resin as the base material is to be analyzed using the light speed $c_{tissue}$ in the actual target, it is rewritten as the following Formula (8).

[Formula 7]
$$I = I_0 \exp(-\mu_{a,resin} c_{resin} t) \quad (7)$$

[Formula 8]
$$I = I_0 \exp\left[-\mu_{a,resin}\left(\frac{c_{resin}}{c_{tissue}}\right) c_{tissue} t\right] \quad (8)$$

The above Formula (8) indicates that the absorption coefficient of the resin is apparently multiplied by $c_{resin}/c_{tissue}$ ($= n_{tissue}/n_{resin}$). As a result, the value of the spectroscopic measurement obtained using the phantom becomes lower than the actual value. The concentrations of the dyes A to C obtained previously (concentration of 0.0206% for the dye A, concentration of 0.0378% for the dye B, concentration of approximately 0% for the dye C) are calculated based on the absorption spectrum of the target before the correction. When the phantom is prepared by containing the dyes A to C in the epoxy resin according to the above concentrations, and the phantom is regarded as the actual target to perform the spectroscopic measurement, the obtained absorption coefficient is a value obtained by multiplying the actual value by $n_{tissue}/n_{resin}$.

Therefore, in the correction step, the absorption spectrum of the target multiplied by $n_{resin}/n_{tissue}$ (=1.15) is set as the corrected absorption spectrum. In the corrected absorption spectrum, the absorption coefficient at a wavelength of 760 nm is 0.0754/cm, the absorption coefficient at a wavelength of 800 nm is 0.0640/cm, and the absorption coefficient at a wavelength of 830 nm is 0.0771/cm. When the concentration of each dye capable of reproducing the corrected absorption spectrum is calculated, the concentration of the dye A is 0.0239%, the concentration of the dye B is 0.0441%, and the concentration of the dye C is approximately 0%. In the phantom prepared by containing the respective dyes in the epoxy resin according to the above concentrations, the absorption coefficient at a wavelength of 760 nm is 0.0658/cm, the absorption coefficient at a wavelength of 800 nm is 0.0559/cm, and the absorption coefficient at a wavelength of 830 nm is 0.0673/cm.

FIG. 6 is a table showing the absorption coefficients at respective wavelengths, the oxygenated hemoglobin concentration ($O_2Hb$), the deoxygenated hemoglobin concentration (HHb), the total hemoglobin concentration (tHb), and the tissue oxygen saturation ($StO_2$) for each of the target (breast) and the actually prepared phantom. These values are obtained as measured by the time resolved spectroscopic apparatus TRS-21 manufactured by Hamamatsu Photonics K. K. From this result, it can be confirmed that the phantom prepared as an example can reproduce the absorption coefficients and the hemoglobin concentrations close to those of the actual living tissue.

Figure 7:
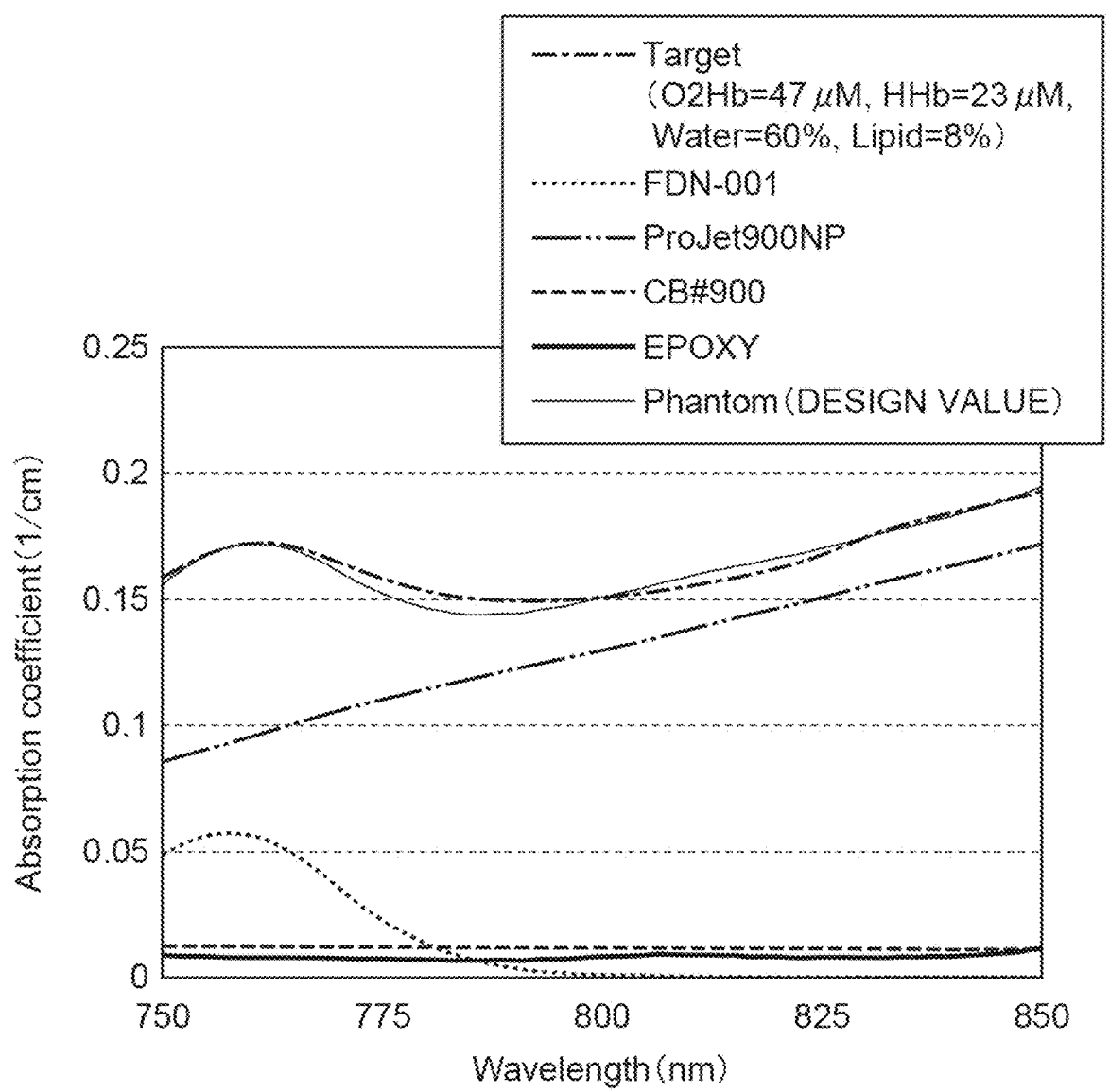
FIG. 7 is a diagram showing absorption spectra of the target (head of normal-oxygen condition), the phantom, the epoxy resin, and the dyes A to C.

FIG. 7 and FIG. 8 show the results when the target of the spectroscopic measurement is a human head (normal-oxygen condition). The human head of the normal-oxygen condition generally contains 47 μM oxygenated hemoglobin ($O_2Hb$), 23 μM deoxygenated hemoglobin (HHb), 60% water, and 8% lipid.

FIG. 7 is a diagram showing absorption spectra of the target (head in normal-oxygen condition), the phantom, the epoxy resin, and the dyes A to C. FIG. 8 is a table showing the absorption coefficients at respective wavelengths, the oxygenated hemoglobin concentration ($O_2Hb$), the deoxygenated hemoglobin concentration (HHb), the total hemoglobin concentration (tHb), and the tissue oxygen saturation ($StO_2$) for each of the target (head in normal-oxygen condition) and the actually prepared phantom.

Figure 9:
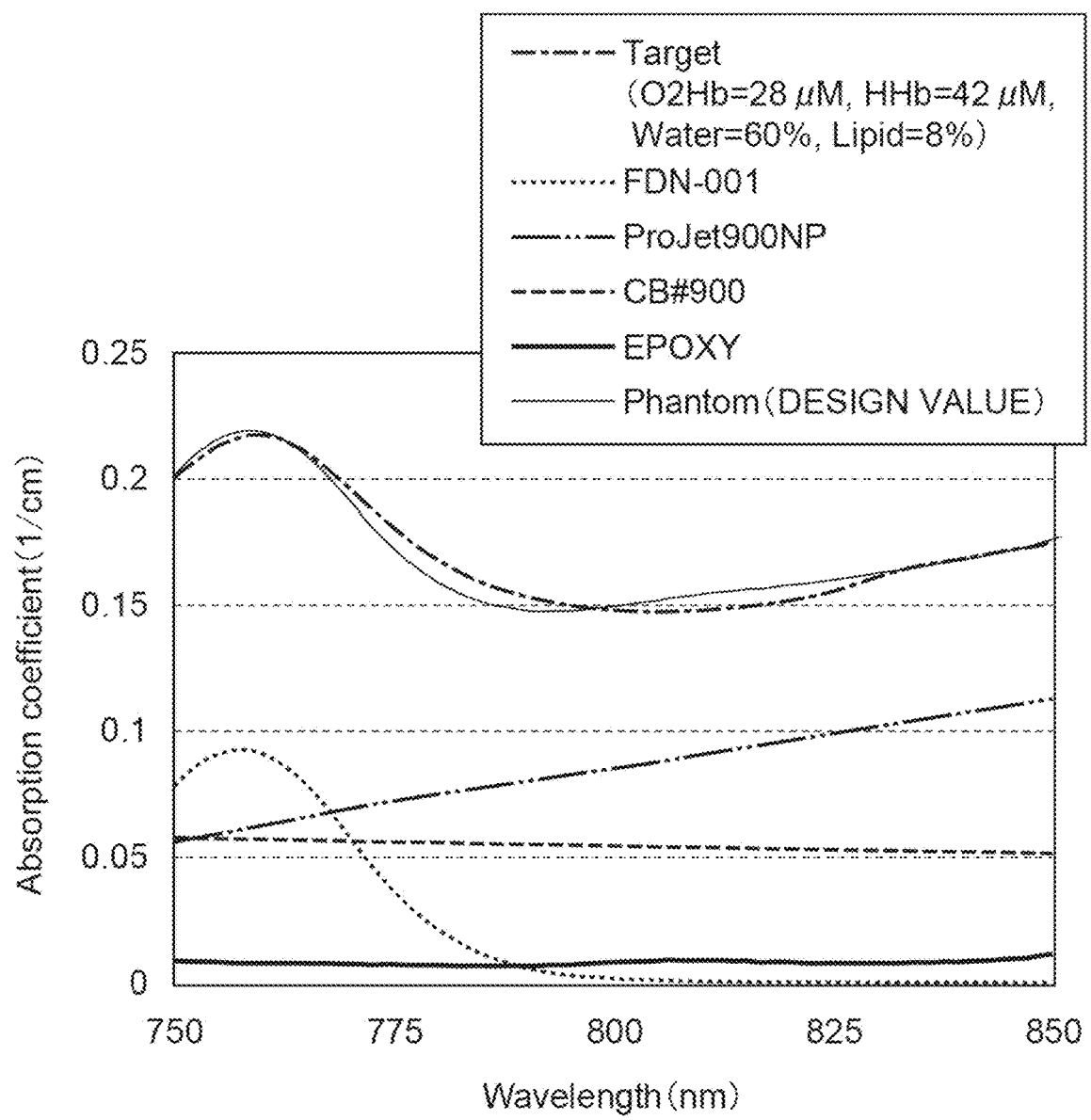
FIG. 9 is a diagram showing absorption spectra of the target (head of low-oxygen condition), the phantom, the epoxy resin, and the dyes A to C.

FIG. 9 and FIG. 10 show the results when the target of the spectroscopic measurement is a human head (low-oxygen condition). The human head of the low-oxygen condition generally contains 28 μM oxygenated hemoglobin ($O_2Hb$), 42 μM deoxygenated hemoglobin (HHb), 60% water, and 8% lipid.

FIG. 9 is a diagram showing absorption spectra of the target (head in low-oxygen condition), the phantom, the epoxy resin, and the dyes A to C. FIG. 10 is a table showing the absorption coefficients at respective wavelengths, the oxygenated hemoglobin concentration ($O_2Hb$), the deoxygenated hemoglobin concentration (HHb), the total hemoglobin concentration (tHb), and the tissue oxygen saturation ($StO_2$) for each of the target (head in low-oxygen condition) and the actually prepared phantom.

For each of the above targets, the phantom prepared as the example can reproduce the absorption coefficients and the hemoglobin concentrations close to those of the actual living tissue.

In the phantom prepared in the present embodiment, by containing the plurality of dyes in the resin, it is possible to reproduce any hemoglobin concentration and tissue oxygen saturation, and thus, it is possible to eliminate complexity and instability due to the use of actual blood, and it is possible to perform simple and highly reproducible evaluation of the apparatus. Further, the phantom is designed and prepared by calculating the concentration of each dye contained in the resin of the base material in consideration of the difference in refractive index between the living tissue as the target of the spectroscopic measurement and the resin as the base material of the phantom, and thus, the performance of the near infrared spectrometer can be more accurately evaluated.

The phantom design method, the phantom preparation method, the phantom design apparatus, the program, and the recording medium are not limited to the embodiments and configuration examples described above, and various modifications are possible.

The phantom design method of the above embodiment is a method for designing a phantom used in evaluating performance of a near infrared spectrometer, and includes (1) a correction step of correcting an absorption spectrum of a target of spectroscopic measurement by the near infrared spectrometer based on a refractive index of the target and a refractive index of a resin used as a base material of the phantom to generate a corrected absorption spectrum; and (2) a calculation step of calculating, based on an absorption spectrum of the resin and an absorption spectrum of each of N types of dyes, N being 2 or more, a concentration of each of the N types of dyes to be contained in the base material such that an absorption spectrum of the phantom constituted by the base material containing the N types of dyes approximates the corrected absorption spectrum in a predetermined wavelength range of a near infrared region.

In the above design method, in the calculation step, a coincidence degree between the absorption spectrum of the phantom constituted by the base material containing the N types of dyes with the calculated concentrations and the corrected absorption spectrum may be obtained.

Further, in the calculation step, for each group including any N types of dyes out of M types of dyes, M being 3 or more, the concentration of each of the N types of dyes to be contained in the base material may be calculated and the coincidence degree may be obtained, and the N types of dyes and the concentrations of any one group may be selected based on the number of types of dyes and the coincidence degree of each group.

In the above design method, the predetermined wavelength range in the calculation step may include a range of 750 nm to 850 nm.

The phantom preparation method of the above embodiment includes calculating the concentration of each of the N types of dyes in the base material by the phantom design method of the above configuration; and preparing the phantom by causing the base material to contain the N types of dyes according to the calculated concentrations.

In the above preparation method, the phantom may be prepared by causing the base material to contain scattering particles in addition to the N types of dyes.

The program of the above embodiment is a program for causing a computer to execute the correction step and the calculation step of the phantom design method of the above configuration. Further, the recording medium of the above embodiment is a computer readable recording medium recording the above program.

The phantom design apparatus of the above embodiment is an apparatus for designing a phantom used in evaluating performance of a near infrared spectrometer, and includes (1) a correction unit for correcting an absorption spectrum of a target of spectroscopic measurement by the near infrared spectrometer based on a refractive index of the target and a refractive index of a resin used as a base material of the phantom to generate a corrected absorption spectrum; and (2) a calculation unit for calculating, based on an absorption spectrum of the resin and an absorption spectrum of each of N types of dyes, N being 2 or more, a concentration of each of the N types of dyes to be contained in the base material such that an absorption spectrum of the phantom constituted by the base material containing the N types of dyes approximates the corrected absorption spectrum in a predetermined wavelength range of a near infrared region.

In the above design apparatus, the calculation unit may obtain a coincidence degree between the absorption spectrum of the phantom constituted by the base material containing the N types of dyes with the calculated concentrations and the corrected absorption spectrum.

Further, the calculation unit may calculate, for each group including any N types of dyes out of M types of dyes, M being 3 or more, the concentration of each of the N types of dyes to be contained in the base material and obtain the coincidence degree, and select the N types of dyes and the concentrations of any one group based on the number of types of dyes and the coincidence degree of each group.

In the above design apparatus, the predetermined wavelength range in the calculation unit may include a range of 750 nm to 850 nm.

INDUSTRIAL APPLICABILITY

The embodiments can be used as a phantom design method and a phantom design apparatus capable of designing a phantom suitably used in evaluating performance of a near infrared spectrometer, a method for preparing the phantom, a program of the phantom design method, and a recording medium recording the program.

REFERENCE SIGNS LIST

10—phantom design apparatus, 11—correction unit, 12—calculation unit, 13—input unit, 14—display unit, 15—storage unit, 20—recording medium.

The invention claimed is:

1. A phantom design method for designing a phantom used in evaluating performance of a near infrared spectrometer, the method comprising:
performing a correction of correcting an absorption spectrum of a target of spectroscopic measurement by the near infrared spectrometer based on a refractive index of the target and a refractive index of a resin used as a base material of the phantom to generate a corrected absorption spectrum; and
performing a calculation of calculating, based on an absorption spectrum of the resin and an absorption spectrum of each of N types of dyes, N being 2 or more, a concentration of each of the N types of dyes to be contained in the base material such that an absorption spectrum of the phantom constituted by the base material containing the N types of dyes approximates the corrected absorption spectrum in a predetermined wavelength range of a near infrared region.

2. The phantom design method according to claim 1, wherein, in the calculation, a coincidence degree between the absorption spectrum of the phantom constituted by the base material containing the N types of dyes with the calculated concentrations and the corrected absorption spectrum is obtained.

3. The phantom design method according to claim 2, wherein, in the calculation, for each group including any N types of dyes out of M types of dyes, M being 3 or more, the concentration of each of the N types of dyes to be contained in the base material is calculated and the coincidence degree is obtained, and the N types of dyes and the concentrations of any one group are selected based on the number of types of dyes and the coincidence degree of each group.

4. The phantom design method according to claim 1, wherein the predetermined wavelength range in the calculation includes a range of 750 nm to 850 nm.

5. A phantom preparation method comprising:
calculating the concentration of each of the N types of dyes in the base material by the phantom design method according to claim 1; and
preparing the phantom by causing the base material to contain the N types of dyes according to the calculated concentrations.

6. The phantom preparation method according to claim 5, wherein the phantom is prepared by causing the base material to contain scattering particles in addition to the N types of dyes.

7. A program for causing a computer to execute the correction step and the calculation step of the phantom design method according to claim 1.

8. A computer readable recording medium recording the program according to claim 7.

9. A phantom design apparatus for designing a phantom used in evaluating performance of a near infrared spectrometer, the apparatus comprising:
a processor configured to
perform a correction of correcting an absorption spectrum of a target of spectroscopic measurement by the near infrared spectrometer based on a refractive index of the target and a refractive index of a resin used as a base material of the phantom to generate a corrected absorption spectrum; and
perform a calculation of calculating, based on an absorption spectrum of the resin and an absorption spectrum of each of N types of dyes, N being 2 or more, a concentration of each of the N types of dyes to be contained in the base material such that an absorption spectrum of the phantom constituted by the base material containing the N types of dyes approximates the corrected absorption spectrum in a predetermined wavelength range of a near infrared region.

10. The phantom design apparatus according to claim 9, wherein, in the calculation, the processor is configured to obtain a coincidence degree between the absorption spectrum of the phantom constituted by the base material containing the N types of dyes with the calculated concentrations and the corrected absorption spectrum.

11. The phantom design apparatus according to claim 10, wherein, in the calculation, the processor is configured to calculate, for each group including any N types of dyes out of M types of dyes, M being 3 or more, the concentration of each of the N types of dyes to be contained in the base material and obtain the coincidence degree, and select the N types of dyes and the concentrations of any one group based on the number of types of dyes and the coincidence degree of each group.

12. The phantom design apparatus according to claim 9, wherein the predetermined wavelength range in the calculation includes a range of 750 nm to 850 nm.

13. The phantom design apparatus according to claim 9, further comprising:
   a storage configured to store a program that causes the processor to execute the correction and the calculation.

* * * * *